United States Patent [19]
Honore et al.

[11] Patent Number: 4,812,458
[45] Date of Patent: Mar. 14, 1989

[54] 6,7-DISUBSTITUTED-2,3-DIHYDROX-YQUINOXALINE COMPOUNDS, PHARMACEUTICAL COMPOSITIONS THEREOF, AND THEIR USE AS NEUROLEPTICS

[75] Inventors: Tage Honoré, Måløv; Jørgen Drejer, Brønshøj; Poul Jacobsen, Rødovre; Flemming E. Nielsen, Virum, all of Denmark

[73] Assignee: A/S Ferrosan, Søborg, Denmark

[21] Appl. No.: 92,034

[22] Filed: Sep. 2, 1987

Related U.S. Application Data

[63] Continuation-in-part of Ser. No. 907,865, Sep. 16, 1986.

[51] Int. Cl.⁴ .................... A61K 31/495; C07D 241/44
[52] U.S. Cl. ..................................... 514/249; 544/354; 544/229
[58] Field of Search ................. 514/249; 544/354
[56] References Cited

U.S. PATENT DOCUMENTS

| | | | |
|---|---|---|---|
| 3,958,011 | 5/1976 | Pigerol et al. | 514/557 |
| 3,962,440 | 6/1976 | St. Clair et al. | 514/249 |
| 3,968,233 | 7/1976 | Garzia | 514/472 |
| 4,657,899 | 4/1987 | Rzeszotarski et al. | 514/114 |
| 4,659,713 | 4/1987 | Hass | 514/249 |

Primary Examiner—Mark L. Berch
Assistant Examiner—E. Bernhardt
Attorney, Agent, or Firm—Gordon W. Hueschen

[57] ABSTRACT

Heterocyclic dihydroxyquinoxaline compounds having the formula

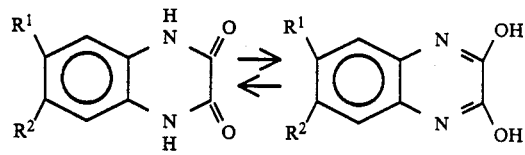

wherein
$R^1$ is halogen, CN, $CF_3$, ethynyl, or $N_3$ and
$R^2$ is $SO_2C_{1-3}$-alkyl, $CF_3$, $NO_2$, ethynyl, or CN.

The invention also relates to a method of preparing the compounds, pharmaceutical compositions thereof, and their use.

The compounds are useful in the treatment of indications caused by hyperactivity of the excitatory neurotransmitters, particularly the quisqualate receptors, and especially as neuroleptics.

8 Claims, No Drawings

6,7-DISUBSTITUTED-2,3-DIHYDROXYQUINOXALINE COMPOUNDS, PHARMACEUTICAL COMPOSITIONS THEREOF, AND THEIR USE AS NEUROLEPTICS

The present application is a continuation-in-part of our prior-filed copending application Ser. No. 907,865, filed Sept. 16, 1986.

The present invention relates to therapeutically active heterocyclic compounds, a method of preparing the same, pharmaceutical compositions comprising the compounds, and a method of treating therewith.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the fast majority of excitatory neurons in the mammalian CNS.

Interaction with glutamic acid mediated neurotransmission is considered as useful approach in the treatment of neurological and psychiatric diseases. Thus, known antagonists of excitatory amino acids have shown potent antiepileptic and muscle relaxant properties (A. Jones et al., Neurosci. Lett. 45, 157–61 (1984) and L Turski et al., Neurosci. Lett. 53, 321–6 (1985)).

It has been suggested that accumulation of extracellular excitatory and neurotoxic amino acids, followed by hyperstimulation of neurons, may explain the neuronal degenerations seen in neurological diseases as Huntingtons chorea, Parkinsonism, epilepsia, senile dementia, and deficiencies of mental and motoric performance seen after conditions of brain ischemia, anoxia and hypoglycemia (E. G. McGree et al., Nature, 263, 517–19 (1976) and R. Simon et al., Science, 226, 850–2 (1984).

Excitatory amino acids exert their actions via specific receptors located postsynaptically or presynaptically. Such receptors are at present conventionally subdivided into three groups based on electrophysiological and neurochemical evidence: 1 the NMDA (N-methyl-D-aspartate) receptors, 2 the quisqualate receptors, and 3 the kainate receptors. L-glutamic acid and L-aspartic acid probably activate all the above types of excitatory amino acid receptors and possibly other types as well.

The consequence of excitatory amino acid interaction with postsynaptic receptors is an increase in intracellular cGMP levels (G. A. Foster et al., Life Sci. 27, 215–21 (1980)) and an opening of Na+-channels (A. Luini et al., Proc. Natl. Acad. Sci. 78, 3250–54 (1981)). Na+-influx in the neurons will depolarize the neuronal membranes, initiate an action potential and ultimately lead to a release of transmitter substance from the nerve terminal. The effects of test compounds on the above mentioned secondary responses to receptor interaction can be tested in simple in vitro systems.

The above mentioned classification of excitatory amino acid receptors into NMDA, quisqualate, and kainate receptors is based primarily on the following electrophysiological and neurochemical findings.

(1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g., 2-amino-5-phosphono-valeric acid (D-APV) and 2-amino-7-phosphonoheptanoic acid (D-APH), while moderate antagonist activity is shown by the D-isomer of long chain 2-amino dicarboxylic acids (e.g., D-2-amino-adipic acid) and long chain diaminodicarboxylic acids (e.g., diaminopimelic acid). The NMDA-induced synaptical responses have been extensively investigated in the mammalian CNS, especially in the spinal cord (J. Davies et al., J. Physiol. 297, 621–35 (1979) and the responses have been shown to be strongly inhibited by $Mg^{2+}$.

(2) Quisqualate receptors are activated selectively by quisqualic acid, other potent agonists being AMPA (2-amino-3-hydroxy-5-methyl-4-isoxazolepropionic acid ) and L-glutamic acid. Glutamic acid diethyl ester (GDEE) is a selective but very weak antagonist of this site. Quisqualate receptors are relatively insensitive to $Mg^{2+}$.

It is well known that an excitatory aminoacid projection from prefrontal cortex to nucleus accumbens (a special part of the forebrain having dopamine neurons) exists (Christie et al., J. Neurochem. 45, 477–82 (1985)). Further it is well known that glutamate modulates the dopaminergic transmission in the striatum (Rudolph et al., Neurochem. int. 5, 479–86 (1983)) as well as the hyperactivity connected with presynaptic stimulation of the dopamine system with AMPA in nucleus accumbens (Arnt. Life Sci. 28, 1597–1603 (1981)).

Quisqualate antagonists are therefore useful as a new type of neuroleptic.

(3) Kainate receptors. Excitatory responses to kainic acid are relatively insensitive to antogonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–91 (1981)) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

Quisqualate receptor binding may be studied by using $^3$H-AM-PA as radioligand.

The influence of glutamic acid analogues on secondary effects of glutamate receptor interactions, such as on c-GMP formation and on Na+-efflux, may be studied in vitro by using brain slices. Such experiments will provide information as to the efficacies (agonist/antagonist) of the test substances. This is in contrast to binding studies, which only provide information on the affinities of the compounds for the receptor.

From U.S. Pat. No. 3,992,378 it is well known that 6,7-dimethyl-2,3-dihydroxyquinoxaline and some mono and some 5,7-disubstituted 2,3-dihydroxyquinoxaline compounds have hypnotic activity.

6-chloro-7-carboxy-2,3-dihydroxyquinoxaline is described as having activity against peptic ulcers in ZA 67/7613.

6-methyl-7-carboxy-2,3-dihydroxyquinoxaline (Biochemistry, 6(11), 3602-8 (1967)), 6-methyl-7-methoxy-2,3-dihydroxyquinoxaline (JP 45/25387), 6-amino-7-nitro-2,3-dihydroxyquinoxaline (DE 2451049), 6-nitro-7-methoxy-2,3-dihydroxyquinoxaline (PL 91909), 6-amino-7-methoxy-2,3-dihydroxyquinoxaline (PL 93835), 6-amino-7-methyl-2,3-dihydroxyquinoxaline (PL 93835), and 6-amino-7-carbomethoxy-2,3-dihydroxyquinoxaline (DE 3106111) are described as having various industrial and research uses.

6-amino-7-chloro-2,3-dihydroxyquinoxaline is disclosed in DE 2847285 as an intermediate in the preparation of azo dyes.

It has now been found that the heterocyclic compounds of the invention have affinity for the quisqualate receptors and are antagonists in connection with this type of receptor which makes them useful in the treatment of any of the numerous indications caused by hyperactivity of excitatory amino acids and more specifically as neuroleptics.

The heterocyclic compounds of the invention have the general formula I

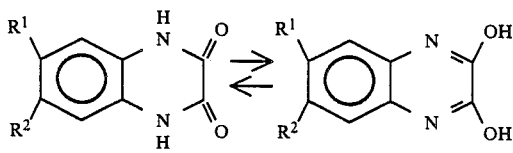

wherein $R^1$ is halogen, CN, $CF_3$, ethynyl, or $N_3$ and $R^2$ is $SO_2C_{1-3}$-alkyl, $CF_3$, $NO_2$, ethynyl, or CN.

The invention also relates to a method of preparing the above-mentioned compounds. This method comprises (a) reacting a compound having the formula II

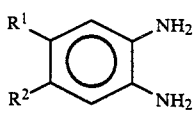

wherein $R^1$ and $R^2$ have the meanings set forth above with oxalate or a reactive derivative thereof to form a compound of formula I, or (b) nitrating a compound having the formula III

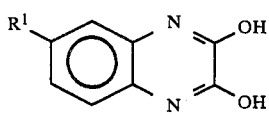

wherein $R^1$ has the meaning set forth above, to form a compound of formula I, wherein $R^2$ is $NO_2$, or (c) reacting a compound having the formula IV

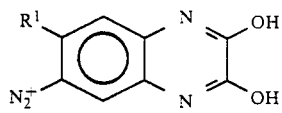

wherein $R^1$ has the meaning set forth above, with potassium tetracyanonickelate to form a compound of formula I, wherein $R^2$ is CN, or (d) reacting a compound having the formula V

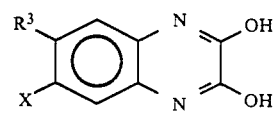

wherein $R^3$ is halogen, CN, $CF_3$, $N_3$, $SO_2C_{1-3}$-alkyl, or $NO_2$, and wherein X is halogen, with trialkylsilylacetylene, and hydrolyzing the compound thus formed, to form a compound of formula I, or (e) reducing a compound having the formula VI

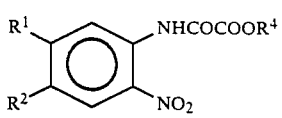

wherein $R^1$ and $R^2$ have the meanings set forth above, and wherein $R^4$ is alkyl, to form a compound of formula I.

The pharmacological properties of the compounds of the present invention can be illustrated by determining their capability for displacing radioactively labelled 2-amino-3-hydroxy-5-methyl-4-isoxazolepropionic acid (AMPA) from the quisqualate type receptors. The antagonistic properties of the compounds is demonstrated by their capability to antagonize quisqualic acid stimulated $Na^+$-efflux from rat striatal slices.

The displacement activity of the compounds may be shown by determining the $IC_{50}$ value which represents the concentration ($\mu$g/ml) which causes a displacement of 50% of the specific binding of $^3H$-AMPA.

The antagonism is measured by determining the $EC_{50}$ value which represents the concentration which reduces the rate of quisqualic acid stimulated sodium efflux by 50%.

H-AMPA binding

500 $\mu$l of thawed rat cerebal cortical membrane homogenate in Tris-HCl (30 mM), $CaCl_2$ (2.5 mM) and KSCN (100 nM) pH 7.1 were incubated at 0° C. for 30 min. with 25 $\mu$l $^3H$-AMPA (5 nM final concentration) and the test compound and buffer. Nonspecific binding was determined by incubation with L-glutamic acid (600 $\mu$M final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Antagonism of quisqualic acid induced $^{22}Na^+$-release

Slices from rat striatum were preincubated with $^{22}Na^+$ for 30 min. After the $^{22}Na^+$ loading period, the slices were successively and every minute transferred through a series of tubes, each containing 1.5 ml of a non-radioactive physiological solution saturated with $O_2$, with the help of a basket shaped sieve. Quisqualic acid (2 μg/ml) was present in the last 5 tubes and the compound to be tested was present in the same 5 tubes plus 3 tubes before. The amount of radioactivity in each washout tube as well as that left in the slices at the end of the experiment was measured by scintillation counting. $EC_{50}$-values were calculated by Hill analysis from at least three different concentrations of test compound as the concentration of test compound which reduces the efflux rate of $^{22}Na^+$-ions to 50% of the efflux rate in the absence of test compound.

Test results obtained by testing some compounds employed in the present invention will appear from the following table 1.

TABLE 1

| $R^1$ | $R^2$ | $IC_{50}$ g/ml | $EC_{50}$ g/ml |
| --- | --- | --- | --- |
| Cl | CN | 0.82 | |
| CN | $NO_2$ | 0.06 | 0.7 |
| Cl | $NO_2$ | 0.43 | 3.0 |
| $N_3$ | $NO_2$ | 0.26 | 3.0 |
| $CF_3$ | CN | 0.39 | |

The invention will now be described in further detail with reference to the following examples.

EXAMPLE 1

6-Bromo-2,3-dihydroxy-7-nitroquinoxaline

To a solution of 0.5 g (2.1 mmol) of 6-bromo-2,3-dihydroxy quinoxaline in 5 ml of concentrated sulfuric acid is added at 0° C. 210 mg (2.1 mmol) $KNO_3$. The solution is stirred at 0° C. for 30 min. and at 24° C. for 3 h. The reaction mixture is poured into ice-water giving 5 g precipitate. The crude product is dissolved in 30 ml of hot 2N NaOH. 4N HCl is added ajusting pH to 2 giving 0.4 g (67%) of 6-bromo-2,3-dihydroxy-7-nitro-quinoxaline, m.p. >300° C.

NMR: two singlets (ppm 7.3 and 7.7 downfield from TMS).

EXAMPLE 2

6-Cyano-2,3-dihydroxy-7-nitroquinoxaline 1 g 6-Cyano-2,3-dihydroxyquinoxaline is added gradually to 10 ml of ice-cooled fuming nitric acid. The mixture is stirred at 25° C. for 1 h. The reaction mixture is poured into ice-water giving 1 g of a crude product. Recrystallization (DMF-water) gives 0.9 g (75%) of 6-cyano-2,3-dihydroxy-7-nitroquinoxaline, m.p. >300° C. IR: peak at 2240 $cm^{-1}$, NMR: two singlets (ppm 7.7 and 8.2 downfield from TMS).

EXAMPLE 3 a: 6-Azido-2,3-dihydroxyquinoxaline

A solution of 5 g (23.5 mmol) 6-amino-2,3-dihydroxyquinoxaline hydrochloride in 250 ml 0.5N $H_2SO_4$ is ice-cooled and then a solution of 1.65 g (24 mmol) $NaNO_2$ in 50 ml water is added. After stirring at 0° C. for 15 min., a solution of 1.5 g (24 mmol) $NaN_3$ in 100 ml water is added. Stirring at 0° C. for 45 min. gives a precipitate of 3 g (67%) 6-azido-2,3-dihydroxyquinoxaline.

IR: a peak at 2220 $cm^{-1}$.

b: 6-Azido-2,3-dihydroxy-7-nitroquinoxaline 2 g 6-azido-2,3-dihydroxyquinoxaline is suspended in 100 ml glacial acetic acid. To the suspension is added 16 ml fuming nitric acid at 24° C. The mixture is stirred at 24° C. for 4 h giving a precipitate of 1.9 g (78%) 6-azido-2,3-dihydroxy-7-nitroquinoxaline.

IR: a peak at 2120 $cm^{-1}$.

NMR: two singlets (ppm 7.0 and 7.7 downfield from TMS).

EXAMPLE 4

2,3-Dihydroxy-6-nitro-7-trifluoromethylquinoxaline

A solution of 1 g (4.4 mmol) 2,3-dihydroxy-6-trifluoromethylquinoxaline in 10 ml concentrated $H_2SO_4$ is ice-cooled and 438 mg (4.4 mmol) $KNO_3$ is added. The mixture is stirred at 0° C. for 0.5 and at 24Z° C. for 3 h. The reaction mixture is poured into ice-water to give 1.02 g. The crude product is dissolved in 2N NaOH. Addition of 4N HCl to pH 5 gives 0.86 g (72%) 2,3-dihydroxy-6-nitro-7-trifluoromethylquinoxaline, m.p. >300° C.

NMR: two singlets (ppm 7.5 and 7.8 downfield from TMS).

EXAMPLE 5

6-Cyano-2,3-dihydroxy-7-trifluoromethylquinoxaline

To a solution of 680 mg (2.5 mmol) 2,3-dihydroxy-6-nitro-7-trifluoromethylquinoxaline in 2 ml concentrated HCl is added at 24° C. a solution of 1.89 g (8 mmol) $SnCl_2-2H_2O$ in 4 ml concentrated HCl. The mixture is stirred at 70° C. for 1 h. Addition of 10 ml $H_2O$ and 50% aqueous NaOH to pH 1 gives a precipitate (1.5 g) which on TLC ($CHCl_3-CH_3OH$ 4:1) shows only one spot. The crude product is dissolved in 5 ml concentrated HCl. To the solution is added 60 ml $H_2O$, and at 0° C. a solution of 170 mg (2.5 mmol) $NaNO_2$ in 5 ml $H_2O$ is added. After stirring at 0° C. for 20 min. saturated $NaHCO_3$ is added to pH 7 followed by a solution of 1.2 g. $K_2Ni(CN)_4$ in 30 ml $H_2O$. The mixture is stirred at 24° C. for 3 h. The reaction mixture is evaporated, and the residue is triturated with acetone to give 200 mg of a crystalline product. Column chromatography (eluent: ethyl acetate containing 5% acetic acid) gives 100 mg (16%) 6-cyano-2,3-dihydroxy-7-trifluoromethylquinoxaline, m.p. >300° C.

IR: a peak at 2240 cm−1.

HMR: two singlets (ppm 7.5 and 7.6 downfield from TMS).

EXAMPLE 6

6-Chloro-7-methylsulfonyl-2,3-dihydroxyquinoxaline

A solution of 8 g methyl-(2-chloro-5-nitro)phenyl-sulfone (Dickey et al., Ind. Eng. Chem. 45, 1730–33(1953)) in 20 ml acetone and 100 ml ethanol is hydrogenated at atm. pressure and at 24° C. by using a Ra-Ni catalyst (3 g). Evaporation gives a TLC-pure product. A solution of the crude product in 100 ml acetic anhydride is stirred at 100° C. for 15 min. and at 24° C. for 3 h. The mixture is poured into 500 ml water giving 5.5 g N-acetyl-4-chloro-5-methyl-sulfonylaniline. 4.7 g of the crude N-acetyl-4-chloro-5-methylsulfonyl aniline is added gradually to 35 ml fuming nitric acid 0°–5° C. After stirring at 24° C. for 45 min. 100 ml ice-water is added, and the mixture is extracted with 3×100 ml ethyl acetate giving 4 g of a mixture of two compounds (TLC). The compounds are separated using column chromatography:

I: 1,6 g (29%) N-acetyl-2-nitro-4-chloro-5-methylsulfonylaniline,

NMR: two singlets (ppm 8.2 and 8.8 downfield from TMS).

II: 2.0 g (36%) N-acetyl-4-chloro-5-methylsulfonyl-6-nitroaniline,

NMR: two doublets (ppm 7.7 and 8.1 downfield from TMS). J=ca. 9 Hz).

1.6 g N-acetyl-2-nitro-4-chloro-5-methylsulfonylaniline in a mixture of 25 ml 6N HCl and 8 ml ethanol is refluxed for 2 h. The reaction mixture is cooled to 24° C. and 50% NaOH is added to pH 12 which gave 0.9 g (65%) of the deacetylated compound. A solution of the crude product in a mixture of 10 ml 4N HCl and 500 ml methanol is hydrogenated at atm. pressure by using 5% Pt-C (100 mg) as a catalyst. The crude 1,2-diamino compound in a mixture of 20 ml 4N HCl and 1.6 g oxalic acid dihydrate is refluxed for 2.5 h. Cooling to 24° C. gives a precipitate. The crude product is dissolved in 2N NaOH and precipitated with addition of 4N HCl to pH 2–3 to give 0.4 g 6-chloro-7-methylsulfonyl-2,3-dihydroxyquinoxaline, m.p >300° C.

EXAMPLE 7

6-Chloro-2,3-dihydroxy-7-nitroquinoxaline

Finely powdered potassium nitrate (1.01 g, 10 mmol) was added during 5 min. to a stirred solution of 6-chloro-2,3-dihydroxyquinoxaline (1.97 g, 10 mmol) in 50 ml of conc. sulfuric acid at 0° C. (icebath). After 1 h the icebath was removed and stirring was continued for 2½ h at room temperature. The mixture was poured into 200 ml of ice/water and the precipitate was isolated, washed with water, ethanol, and ether. The product was dissolved in 70 ml of hot 2N sodium hydroxide, filtered while hot, and reprecipitated with conc. hypochloric acid to give 2.12 g (88%) of pure title compound; m.p. >300° C.;

IR (KBr): 1705, 1620 cm$^{-1}$;

3H-NMR (DMSO-d6): ppm 7.23(s, 1H, H-5; 7.82(s, 1H, h-8); 12.1 (broad s, 2H, 2NH) downfield from TMS.

EXAMPLE 8

6-Chloro-7-cyano-2,3-dihydroxyquinoxaline

6-Amino-7-chloro-2,3-dihydroxyquinoxaline (0.42 g, 2.0 mmol) was added to 20 ml of stirred, hot 1M hydrochloric acid, and the resulting solution was cooled to 0° C. The finely divided hydrochloride was diazotized at 0°–5° C. with sodium nitrite (0.14 g, 2.0 mmol) in 5 ml of water with vigorous stirring, which was continued for 30 min. A solution of potassium tetracyanonickelate (1.3 g, 5.4 mmol) in 25 ml of saturated aqueous sodium hydrogen carbonate was added to the resulting mixture with stirring at room temperature. After 3 h the mixture was cooled on ice and filtered. The product was washed with water, boiled in a mixture of 2N sodium hydroxide (25 ml) and ethanol (50 ml), and filtered while hot. The filtrate was cooled and acidified to pH 1 with concentrated hydrochloric acid. The resulting precipitate was isolated, washed with water and dried to give 40 mg (9%) of the required product; m.p. >300° C.;

IR (KBr): 2235(CN), 1700 cm$^{-1}$;

$^1$H-HMR(DMSO-d6): ppm 7.24(s, 1H, ArH), 7.43(s, 1H, ArH), 12.1(broad s, 2H, 2NH) downfield from TMS.

EXAMPLE 9 a:
2,3-Dihydroxy-6-trimethylsilylethynyl-7-nitroquinoxaline

A mixture of 500 mg (1,9 mmol) 6-brom-2,3-dihydroxy-7-nitroquinoxaline (ex. 1) in 10 ml dry dimethylformamide and 20 ml dry triethylamine is added 4 mg palladium(II)acetate, 8 mg triphenylphosphine and 600 l (4,3 mmol) trimethylsilylacetylene. The mixture is refluxed for 2.5 h under nitrogen. After cooling to room temperature, the reaction mixture is evaporated in vacuo. The residue is stirred with water, filtered and washed with water to give 500 mg of a crude product. The crude product is dissolved in ethyl acetate and purified by column chromatography (silica gel) to give 400 mg (70%) of 2,3-dihydroxy-6-trimethylsilylethynyl-7-nitroquinoxaline.

NMR (DMSO-d6): ppm 7.8 (1H, s), 7.2 (1H, s), 0.3 (9H, s).

b: 6-Ethynyl-2,3-dihydroxy-7-nitroquinoxaline

A solution of 300 mg (0.99 mmol) 2,3-dihydroxy-6-trimethylsilylethynyl-7-nitroquinoxaline in 10 ml methanol is added 200 mg (1.45 mmol) potassium carbonate and then stirred at room temperature for 1 h. The reaction mixture is evaporated in vacuo and added water and 4N hydrochloric acid to pH 6. The precipitated product is filtered off and washed with water to give 200 mg (88%) of 6-ethynyl-2,3-dihydroxy-7-nitroquinoxaline m.p. >300° C.

NMR (DMSO-d6): ppm 7.7 (1H, s), 7.2 (1H, s), 4.5 (1H, s).

EXAMPLE 10 a. 4-Ethoxyalylaminophthalodiamide

To a solution of 10 g (56,0 mmol) 4-aminophthalodiamide in 200 dry dimethylformamide was added 8,5 ml (61,2 mmol) dry triethylamine. A solution of 7.0 ml (61,5 mmol) ethoxalylchloride in 50 ml dry dimethylformamide was added dropwise. Stirring was continued at 25° C. for 1 h. The reaction mixture was added 600 ml methanol, ice-cooled and the preciptate was filtered off and washed with a little methanol to give 10,6 g (68%) 4-ethoxalylaminophthalodiamide. m.p. 229,0° C.

b. 4-Ethoxalylaminophthalodinitrile

To a mixture of 10 g (35,8 mmol) 4-ethoxalylaminophthalodiamide in 100 ml dry pyridine was gradually added 5,9 ml (64,9 mmol) phosphorus oxychloride. Stirring was continued at 25° C. for 30 min. The reaction mixture was poured into an ice-cooled mixture of 100 ml concentrated hydrochloric acid and 200 ml water to give 6,6 g (76%) 4-ethoxalylaminophthalodinitrile as a precipitate, m.p. 193,7° C.

c. 4-Ethoxalylamino-5-nitrophthalodinitrile

A solution of 5 g (20,6 mmol) 4-ethoxalylaminophthalodinitrile in 75 ml 100% nitric acid was left with stirring at 25° C. for 48 h. The reaction mixture was poured into 500 ml ice-water to give a precipitate (4 g). Column chromatography (silica gel, eluents: toluene containing 25% ethyl acetate) gave 2 compounds: 4-ethoxalylamino-3-nitro-phthalodinitrile (1,9 g);

NMR (DMSO-d$_6$): 8.5 (1H, d, J=8 HZ), 8.3 (1H, d, J=8 HZ) and 4-ethoxalylamino-5-nitrophthalodinitrile (1,9 g);

NMR (DNSO-d$_6$): 9.0 (1H, s), 8.7 (1H, s). The last compound was used in the next step.

d. 6,7-Dicyano-2,3-dihydroxyquinoxaline

A solution of 0,5 g (1,7 mmol) 4-ethoxalylamino-5-nitrophthalodinitrile in a mixture of 50 ml ethanol and 20 ml ethyl acetate was hydrogenated at atm. pressure by using 5% Pd-C (0,5 g) as a catalyst. The reaction mixture was filtered and evaporated in vacuo. The residue was dissolved in ethyl acetate, and the solution was passed through a short column (silica gel) to give the intermediary product 4-amino-5-ethoxalylaminophthalodinitrile. A solution of this compound in 50 ml ethanol was refluxed 3 h to give 0,2 g (53%) 6,7-dicyano-2,3-dihydroxyquinoxaline as crystals, m.p. >300° C.

IR (KBr): 2240 cm$^{-1}$ (CN);

NMR (DMSO-d$_6$): 12.2 (2H, broad m), 7.6 (2H, s).

The pharmaceutical preparations or compositions comprising the compounds of the invention may be administered to humans or animals by oral or parenteral route.

An effective amount of the active compound or pharmaceutically-acceptable salt thereof may be determined in accordance with the usual factors, such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which doe not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 50–200 mg of active ingredient in or together with a pharmaceutically-acceptable carrier per unit dosage.

The dosage of the compounds according to this invention is 1–500 mg/day, e.g., about 100 mg per dose, when administered to patients, e.g., humans, as a drug.

A typical tablet which may be prepared by conventional tabletting techniques contains:

| Core: | | |
|---|---|---|
| Active compound (as free compound or salt thereof) | | 100 mg |
| Colloidal silicon dioxide (Aerosil TM) | | 1.5 mg |
| Cellulose, microcryst. (Avicel TM) | | 70 mg |
| Modified cellulose gum (Ac-Di-Sol TM) | | 7.5 mg |
| Magnesium stearate | | 1 mg |
| Coating: | | |
| HPMC | approx. | 9 mg |
| *Mywacett TM 9–40 T | approx. | 0.9 mg |

*Acylated monoglyceride used as plasticizer for film-coating

The free dihydroxyquinoxaline compounds of the present invention which form alkali metal or alkaline earth metal salts may be employed in such salt form. Such alkali metal or earth alkali metal salts are ordinarily formed by reacting the dihydroxyquinoxaline compound with an equivalent amount or excess of the selected alkali metal or earth alkali metal as the hydroxide, frequently and suitably by admixture in the presence of a neutral solvent, from which the salt may be precipitated or recovered in other conventional manner, e.g., by evaporation. Administration of a compound of the invention is often preferably in the form of a pharmaceutically-acceptable water-soluble alkali metal or earth metal salt thereof, and orally, rectally, or parenterally in the form of a pharmaceutical composition wherein it is present together with a pharmaceutically-acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective neuroleptic, especially quisqualate antagonistic, amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of neuroleptic, particularly quisqualate antagonistic, activity and their low toxicity, together presenting a most favorable therapeutic index, the compounds of the invention may be administered to a subject, e.g., a living animal body, in need of such neuroleptic treatment, elimination, alleviation, or amelioration of an indication which is sensitive to a change in the quisqualate receptor condition, often preferably in the form of an alkali metal or earth alkali metal salt thereof, concurrently, simultaneously, or together with a pharmaceutically-acceptable carrier or diluent, especially and preferably in the form of a pharmaceutical composition thereof, whether by oral, rectal, or parenteral (including subcutaneous) route, in an effective amount. Suitable dosage ranges are 50–200 milligrams daily, preferably 50–100 milligrams daily, and especially 70–100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, and particularly the quisqualate receptors, in a subject in need thereof, which comprises the step of administering to the said subject a neurologically- or neuroleptically-effective amount of a quisqualate antagonistic dihydroxyquinoxaline compound of the invention.

In conclusion, from the foregoing, it is apparent that the present invention provides novel neurologically-effective quisqualate antagonist dihydroxyquinoxaline compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact composition, methods, procedures, or embodiments shown and described, as obvious modifications and equivalents will be apparent to one skilled in the art, and the invention is therefore to be limited only by the full scope of the appended claims.

We claim:

1. A heterocyclic dihydroxyquinoxaline compound having the formula I

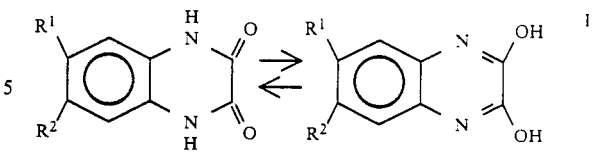

wherein
$R^1$ is halogen, CN, CF$_3$, ethynyl, or N$_3$ and
$R^2$ is SO$_2$C$_{1-3}$-alkyl, CF$_3$, NO$_2$, ethynyl, or CN.

2. A compound of claim 1, wherein $R^1$ is Cl, CN or CF$_3$ and $R^2$ is CN, or NO$_2$.

3. A compound of claim 1, which is 6-cyano-7-nitro-2,3-dihydroxyquinoxaline.

4. A compound of claim 1, which is 6-chloro-7-cyano-2,3-dihydroxyquinoxaline.

5. A compound of claim 1, which is 6-trifluoromethyl-7-cyano-2,3-dihydroxyquinoxaline.

6. A pharmaceutical composition useful as a neuroleptic comprising as active component a neuroleptically-effective amount of a heterocyclic dihydroxyquinoxaline compound according to claim 1 or a pharmaceutically-acceptable salt thereof and a pharmaceutically-acceptable carrier.

7. A pharmaceutical composition according to claim 6 in the form of an oral dosage unit containing about 50–200 mg of the active compound.

8. A method of treating hyperactivity of the excitatory neurotransmitters in a subject in need thereof, which comprises the step of administering to the said subject a neuroleptically-effective amount of a dihydroxyquinoxaline compound of claim 1.

* * * * *

UNITED STATES PATENT AND TRADEMARK OFFICE
CERTIFICATE OF CORRECTION

PATENT NO. : 4,812,458

DATED : March 14, 1989

INVENTOR(S) : Tage Honoré, Jørgen Drejer, Poul Jacobsen and Flemming E. Nielsen

It is certified that error appears in the above-identified patent and that said Letters Patent is hereby corrected as shown below:

Col. 1, line 23; "as" should read -- a --
Col. 1, line 36; "McGree" should read -- McGreer --
Col. 1, line 41; "conventionally" should read -- conveniently --
Col. 2, line 33; "antogonism" should read -- antagonism --
Col. 3, line 55; after "above" insert a comma -- , --
Col. 4, line 50; "H-AMPA" should read -- $^3$H-AMPA --
Col. 4, line 51; "cerebal" should read -- cerebral --
Col. 4, line 53; "nM)" should read -- mM) --
Col. 5, line 42; "5 g" should read -- 0.5 g --
Col. 6, line 22; "24Z°C." should read -- 24°C. --
Col. 7, line 27; "precipitated" should read -- reprecipitated --
Col. 7, line 43; "hypo-" should read -- hydro- --
Col. 7, line 48; "h-8);" should read -- H-8); --
Col. 8, line 2; "$^1$H-HMR(" should read -- $^1$H-NMR( --
Col. 8, line 41; "4-Ethoxyalylaminophthalodiamide" should read -- 4-Ethoxalylaminophthalodiamide --
Col. 8, line 43; "200 dry" should read -- 200 ml dry --
Col. 8, line 48; "preciptate" should read -- precipitate --
Col. 9, line 29; after "or" insert -- a --
Col. 9, line 48; "doe" should read -- do --

UNITED STATES PATENT AND TRADEMARK OFFICE
CERTIFICATE OF CORRECTION

PATENT NO. : 4,812,458

DATED : March 14, 1989

INVENTOR(S) : Tage Honoré, Jørgen Drejer, Poul Jacobsen and Flemming E. Nielsen

It is certified that error appears in the above-identified patent and that said Letters Patent is hereby corrected as shown below:

Col. 10, line 30; after "earth" insert -- alkali --
Col. 11, line 27; "composition," should read -- compositions, --

Signed and Sealed this

Seventeenth Day of April, 1990

Attest:

HARRY F. MANBECK, JR.

Attesting Officer

Commissioner of Patents and Trademarks